US011416513B2

(12) United States Patent
Hussam et al.

(10) Patent No.: US 11,416,513 B2
(45) Date of Patent: Aug. 16, 2022

(54) SEARCHING DATA STRUCTURES MAINTAINED BY DISTRIBUTED DATA SOURCES

(71) Applicant: Universal Research Solutions, LLC, Columbia, MO (US)

(72) Inventors: Ali Adel Hussam, Columbia, MO (US); Nathan Bleigh, Kansas City, MO (US)

(73) Assignee: Universal Research Solutions, LLC, Columbia, MO (US)

( * ) Notice: Subject to any disclaimer, the term of this patent is extended or adjusted under 35 U.S.C. 154(b) by 0 days.

(21) Appl. No.: 16/020,662

(22) Filed: Jun. 27, 2018

(65) Prior Publication Data

US 2020/0004864 A1   Jan. 2, 2020

(51) Int. Cl.
*G06F 16/26* (2019.01)
*G06F 16/438* (2019.01)
*G06F 3/0481* (2022.01)

(52) U.S. Cl.
CPC ............ *G06F 16/26* (2019.01); *G06F 16/438* (2019.01); *G06F 3/0481* (2013.01)

(58) Field of Classification Search
None
See application file for complete search history.

(56) References Cited

U.S. PATENT DOCUMENTS

2009/0048874 A1* 2/2009 Sasano .................. G06Q 10/00
705/3
2009/0248447 A1* 10/2009 Niwa ..................... G16H 15/00
705/3
2010/0171682 A1* 7/2010 Chen ..................... G16H 30/40
345/55

(Continued)

FOREIGN PATENT DOCUMENTS

JP    2005-309863    11/2005
WO   WO2017/134093   8/2017

(Continued)

OTHER PUBLICATIONS

Alexander Rind, "Interactive Information Visualization to Explore and Query Electronic Health Records," Foundations and Trends? In Human-Computer Interaction, vol. 5 (3):207-298 (Jan. 1, 2013).

(Continued)

*Primary Examiner* — Richard L Bowen
(74) *Attorney, Agent, or Firm* — Fish & Richardson P.C.

(57) ABSTRACT

A method includes receiving a query that identifies an entity, obtaining a first set of entity records responsive to the query, wherein each record of the first set of entity records comprises one or more visual objects responsive to the query, obtaining a second set of entity records responsive to the query, wherein each record in the second set of entity records includes an entity score describing the entity that is associated with a period of time when the one or more visual objects were generated, executing computer program code correlating the first set of entity records with the second set of entity records, executing computer program code that uses the second set of entity records with which the first set of entity records is correlated to enhance the first set of entity records, and generating visual snapshot rendering data based on the enhanced first set of entity records.

18 Claims, 4 Drawing Sheets

(56) References Cited

U.S. PATENT DOCUMENTS

| | | | | |
|---|---|---|---|---|
| 2012/0084293 | A1* | 4/2012 | Brown | A61B 5/00 |
| | | | | 707/741 |
| 2013/0209522 | A1* | 8/2013 | Brooks | A61L 27/54 |
| | | | | 424/400 |
| 2017/0091464 | A1* | 3/2017 | Richards | G06F 21/606 |
| 2017/0177795 | A1 | 6/2017 | Mabotuwana et al. | |
| 2018/0181737 | A1* | 6/2018 | Tussy | G06F 21/32 |
| 2018/0365483 | A1* | 12/2018 | Nakagome | G06K 9/00248 |
| 2018/0373941 | A1* | 12/2018 | Kwant | G08G 1/0129 |
| 2019/0164643 | A1* | 5/2019 | Heismann | G16H 30/40 |
| 2019/0228524 | A1* | 7/2019 | Chen | G16H 30/20 |

FOREIGN PATENT DOCUMENTS

| | | | | |
|---|---|---|---|---|
| WO | WO-2017134093 A1 * | 8/2017 | | G06F 19/321 |
| WO | WO 2020/006301 | 1/2020 | | |

OTHER PUBLICATIONS

Notification of Transmittal of International Search Report and Written Opinion for corresponding PCT Application No. PCT/US2019/039608, dated Oct. 14, 2019, pp. 1-16.

Bui A. et al., "TimeLine: Visualizing Integrated Patient Records," IEEE Transactions on Information Technology in Biomedicine, IEEE Service Center, vol. 11(4):462-473 (Jul. 1, 2007).

Hsu W. et al., "Context-Based Electronic Health Record: Toward Patient Specific Healthcare," IEEE Transactions on Information Technology in Biomedicine, IEEE Service Center, vol. 16(2):228-234 (Mar. 1, 2012).

\* cited by examiner

SEARCHING DATA STRUCTURES MAINTAINED BY DISTRIBUTED DATA SOURCES

FIELD

This specification is generally related to searching data structures and more specifically, correlating data structures obtained responsive to the search of the data structures to produce an enhanced visual snapshot of correlated data derived from the searched data structures.

BACKGROUND

Databases can typically store large quantities of information related to entities. Typically, single databases provide one or more records of information related to the entities and no other information can be inferred.

SUMMARY

According to one innovative aspect, the subject matter of this specification may be embodied in a method for generating visual snapshot rendering data that, when rendered by a user device, provides a visual snapshot that describes a historical trend associated with an entity that correlates multiple data records from different distributed data sources into a single user interface of an application. The method may include the actions of receiving, by an application programming interface and from the user device, a query that identifies an entity, obtaining, by the application programming interface, a first set of data structures representing first entity records from a first distributed data source that are responsive to the query, wherein each of the first entity records comprises a visual object that is responsive to the query and associated with a first time when the visual object was generated, obtaining, by the application programming interface, a second set of data structures representing second entity records from a second distributed data source that are responsive to the query, wherein each of the second entity records comprises an entity score that is associated with a second time when the entity score was generated, executing, by the application programming interface, computer program code that correlates the first entity records represented by the first set of data structures from the first distributed data source with the second entity records represented by the second set of data structures from the second distributed data source based on the first time and the second time, executing, by the application programming interface, computer program code that uses the correlated data to enhance the first entity records, and generating, by the application programming interface, visual snapshot rendering data based on the enhanced first entity records.

Other versions include corresponding systems, apparatus, and computer programs to perform the actions of methods, encoded on computer storage devices.

These and other versions may optionally include one or more of the following features. For instance, in some implementations, the entity score, for each of the second entity records, is based on answers provided to questions of a questionnaire.

In some implementations, the visual object includes an image one or more portions of the entity.

In some implementations, executing, by the application programming interface, computer program code that correlates the first entity records represented by the first set of data structures from the first distributed data source with the second entity records represented by the second set of data structures from the second distributed data source based on the first time and the second time comprises: for each particular entity record of the first set of entity records: correlating the particular entity record with one or more of the second entity records from the second distributed database based on a determination that the first time and the second time both fall within a predetermined time period.

In some implementations, in response to generating the visual snapshot rendering data based on the enhanced first entity records, transmitting, by the application programming interface, the visual snapshot rendering data to the user device for display.

In some implementations, receiving, by the application programming interface, a user selection on a plot point of the visual snapshot rendering data for a request for metadata corresponding to a particular visual object and a corresponding time; and transmitting, by the application programming interface, the metadata corresponding to the particular visual object and the corresponding time to the user device for display.

In some implementations, the visual snapshot rendering data is modeled in a 3D format.

BRIEF DESCRIPTION OF THE DRAWINGS

Like reference numbers and designations in the various drawings indicate like elements.

DETAILED DESCRIPTION

Figure 1:
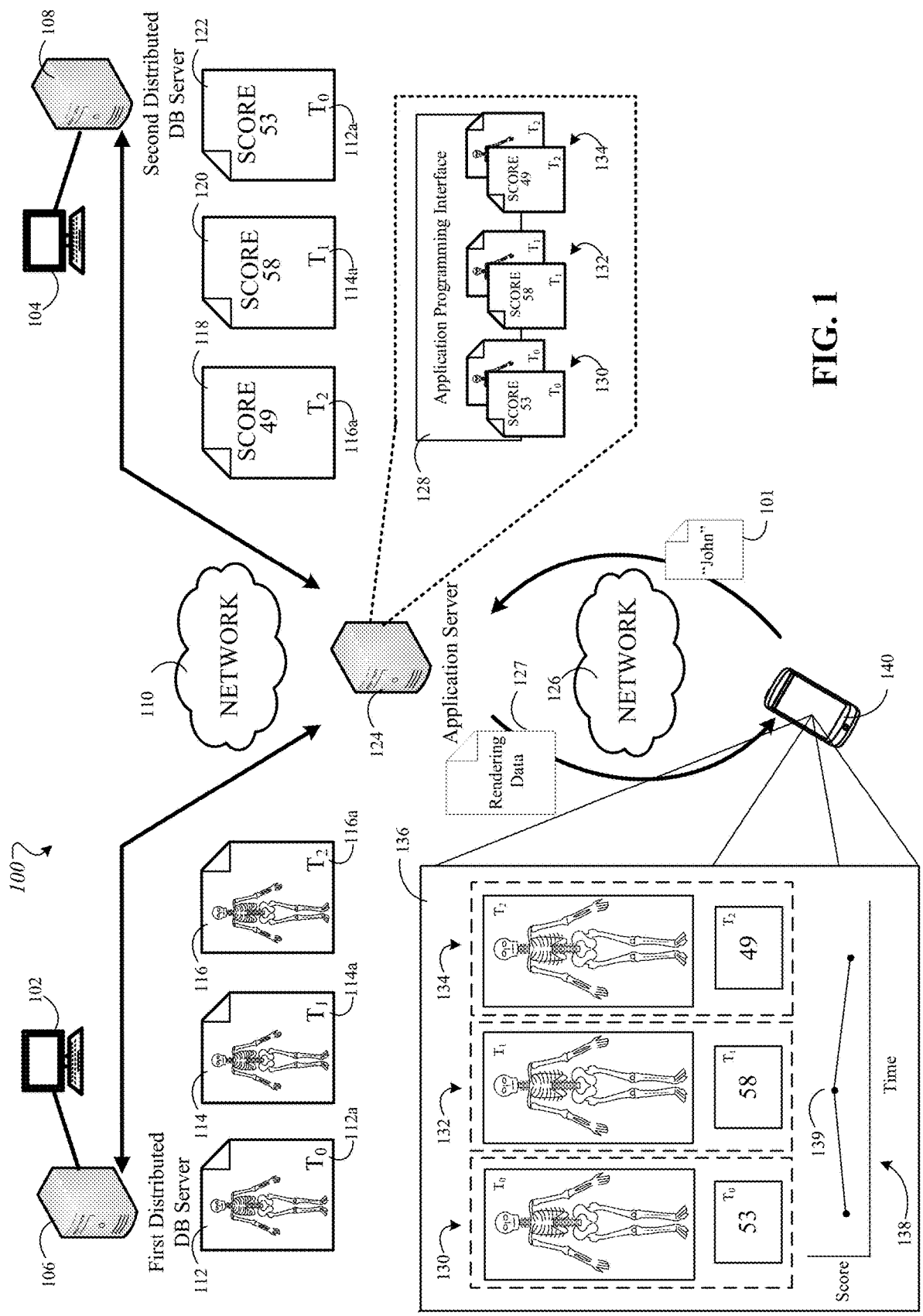
FIG. 1 is a diagram of an example of a system for searching and correlating distributed database records.

FIG. 1 is a diagram of an example of a system 100 for searching and correlating distributed database records. The system 100 includes a first source computer 102, a second source computer 104, a first distributed database (DB) server 106, a second distributed DB server 108, a network 110, an application server 124, a network 126, and a client device 140

The first source computer 102 is configured to communicate with the first distributed DB server 106 via one or more networks such as network 110. The network 110 can be wired or wireless and may include, for example, one or more of a LAN, a WAN, a cellular network, the Internet, or the like. Alternatively, the first source computer 102 may be configured to communicate with the first distributed DB server 106 using one or more other networks.

The first source computer 102 is a computer that can be used to generate visual objects such as visual objects 112, 114, 116. The first source computer 102 may include a smartphone, a smartwatch, a tablet, a laptop, a desktop, a server, a camera, an X-ray machine, a Magnetic Resonance Imaging (MRI) machine, a Computed Tomography (CT) Scan, the like, or any combination thereof. In some implementations, a user may use the first source computer 102 to capture visual objects describing a feature of an entity. For example, the user can use a first source computer to obtain an MRI of an entity. The visual objects obtained by the first source computer 102 may be stored in the first distributed DB 106. The first source computer 102 is configured to communicate with the first distributed DB server 106 via one or more networks such as network 110. Alternatively, the first source computer 102 may be configured to communicate with the first distributed DB server 106 using one or more other networks.

The second source computer 104 is a computer that can be used to generate scores such as scores 118, 120, and 122. The second source computer 104 may include a smartphone, a smartwatch, a tablet, a laptop, a desktop, a server, the like, or any combination thereof. In some implementations, a second source computer 104 can be used to generate a score for an entity. The score may be based on entity responses to one or more questions of a questionnaire. The second source computer 104 is configured to communicate with the second distributed DB server 108 via one or more networks such as network 110. Alternatively, the second distributed computer 104 may be configured to communicate with the second distributed DB server 108 using one or more other networks.

The first distributed DB server 106 can be used to process and store records in a computing system that is close to the records' source computer. For example, the first distributed DB server 106 can be used to access, store, and transmit visual objects such as visual objects 112, 114, 116 that have been generated by the source computer 102. The first distributed DB server 106 may also prepare the visual objects for processing by the application server 124. Preparing the visual object for processing by the application server 124 may include, for example, tagging each respective visual object 112, 114, 116 with a timestamp 112a, 114a, 116a that enables the visual objects 112, 114, 116 to be correlated, by the application server 124, with other data objects. The timestamp may be accessed from metadata generated when the respective visual object 112, 114, 116 were generated using the first source computer 102.

The second distributed DB server 108 can be used to process and store records in a computing system that is close to the records' source computer. For example, the second distributed DB server 108 can be used to access, store, and transmit visual objects such as scores 118a, 120a, 122a that have been generated by the source computer 104. In some implementations, the second distributed DB server may be a server of medical services provider, an insurance company, or the like that has generated scores for entities. In other implementations, the second distributed DB server may be a server of an online patient community storing data relating to patient outcome scores. Such an online patient community is described in more detail in U.S. patent application Ser. No. 13/973,568, which is herein incorporated by reference in its entirety.

The second distributed DB server 108 may also prepare the scores for processing by the application server 124. Preparing the scores for processing by the application server 124 may include, for example, tagging each respective score 118, 120, 122 with a timestamp 118a, 120a, 122a that enables the scores 118, 120, 122 to be correlated, by the application server 124, with other data objects such as the visual objects 112, 114, 116. The respective timestamps may be accessed from metadata generated when the respective scores 118, 120, 122 were generated using the second source computer 104.

The first distributed DB server 106 and the second distributed DB server 108 may include any type of database such as a relational database, a hierarchal database, an unstructured database, an SQL database, or any other kind of database that allows for the storage and retrieval of data. In some implementations, the system 100 includes an application server 124 for communicating with the first distributed DB server 106 and the second distributed DB server 108. In other implementations, the application server 124 can be stored in the first distributed DB server 106 or stored in the second distributed DB server 106. In other implementations, the application server 124 can be stored in the client device 140. The application server 124 can include one or more computers connected locally or over a network. The application server 124 can communicate with the first distributed DB server 106 and the second distributed DB server 108 over network 110.

The application server 124 includes an application programming interface (API) 128. The API 128 includes one or more software subroutines to allow applications existing on the application server 124 to communicate with the client device 140, the first distributed DB server 106, and the second distributed DB server 108. In addition, the API 128 correlates any data received from each of these devices. The API 128 can also be used to generate rendering data to provide to a client device based on data correlated by the API 128 from multiple distributed DV servers 106, 108.

In particular, the application server 124 can transmit a request for a first set of entry records at the first distributed DB server 106. Additionally, the application server 124 can transmit a second request for a second set of entity records at the second distributed DB server 108. In another instance, the first distributed DB server 106 and the second distributed DB server 108 can transmit a first set of entry records and a second set of entry records, respectively, to the application server 124 on a periodic basis without request from the application server 124. For example, the periodic basis can be hourly, daily, weekly, or monthly. In some implementations, the application server may transmit a request for information to both the first distributed DB 106 and the second distributed DB 108 responsive to request for information about an entity from a user.

The application server 124 is configured to receive one or more requests or queries from a client device 140 over network 126. The client device 140 can be, for example, a cell phone, laptop computer, desktop computer, a laptop computer, a tablet computer, a wearable computer, a cellular phone, a smart phone, a music player, an e-book reader, a navigation system, or any other appropriate computing devices.

In some implementations the source computer 104 may be to present a questionnaire to a user. The questionnaire may include a plurality of questions related to a user's medical condition, a user's medical treatment, a user's medical history, or the like. A user can use the second source computer 104 to provide answers to the questions provided in the questionnaire. In some implementations, the second source computer 104 may generate a score based on the user's answers to the questions in the questionnaire. Alternatively, the source computer 104 may provide the completed questionnaire to the second distributed DB server 108 and the second distributed DB server 108 may perform operations to generate a score based on the answer to the questions in the questionnaire.

In yet other examples, the source computer 104 or the second distributed DB server 108 may receive a completed questionnaire over a network from another computer. The source computer 104 or the second distributed DB server 108 may then generate a score that is based on the answers to questions in the received questionnaire.

Generation of a score for a questionnaire includes the second source computer 104 processing the received patient questionnaire. For example, the second source computer 104 may extract the answers from the received questionnaire and generate one or more scores for user that provided the answers to the questions of the questionnaire based on the extracted answers. For instance, the questionnaire can ask questions such as "What is your main problem?", "To what extent does this problem affect your daily activity (work, sleeping, eating, etc.)?", and "Has the problem improved since you first noticed symptoms?" These questions relate to a level of functionality with respect to a user's body part, such as for example, arm, shoulder, neck, ankle, or rotator cuff. The source computer 104 can analyze the answers provided by the patient and determines a particular score based on the extracted answers. The scores may be determined based on predetermined weights assigned to particular question-answer combinations.

By way of example, the source computer 104 may determine, based on answers to questions of a questionnaire related to an entity's ankle, an entity score of "53". Such a score can indicate that the entity's ankle works slightly more than average according to the questionnaire. In general, the better the entity's particular body part is feeling and functioning, the higher the particular score for the entity. In response, the source computer 104 may store the extracted answers of the entity questionnaire and the determined score for the entity in the second distributed DB server 108.

Accordingly, the generated score is a measure that can be used to represent characteristics of a particular entity at a particular time. For example, the score can provide an indication of the health of an entity for a particular condition, treatment, or the like at the particular time that the questionnaire was completed.

In some implementations, the second distributed DB server 108 may index the stored questionnaire in the second distributed DB server 108 using data representative of an entity. Data representative of the entity can include the entity's name, an entity identifier (e.g., P132), one or more keywords retrieved from the received questionnaire, and a particular ID to reference the questionnaire. As such, the questionnaire is stored in a memory location of the second distributed DB server 108 and other computers such as the application server 124 can subsequently use one or more of the types of data representative of the entity to retrieve the questionnaire and additional data form the second distributed DB server 108. The data representative of the entity can include a name of the entity, as described above.

With respect to the particular example of FIG. 1, the application server 124 can process a request from the client device 140 that includes data representing an entity. For instance, the data can be a representation of a name of the entity, such as an acronym representing the name. In another example, the data representing the entity can include a code word, such as one or more numbers to represent the entity in the request. The client device 140 can generate a coded representation of the request to send over network 126 for bandwidth efficiency purposes.

The application server 124 can process the received request from a client device 140 to identify an entity from the request. For example, as illustrated in FIG. 1, a user, such as a patient or a doctor, can enter a request 101 in an application of the client device 140 for viewing visual snapshot data corresponding to the entity "John." The client device 140 transmits the request 101 to the application server 124 and processes the request 101. The application server 124 analyzes the request 101 to retrieve the text string "John" to identify one or more candidate entry names. For example, if the request included the text string "John Rock," the one or more candidate entry names included "John" and "Rock." In addition, the application server 124 analyzes the one or more candidate entry names to determine a context of the one or more candidate entry names. For example, if the one or more candidate entry names included "John" and "Rock," the application server 124 can determine these two names correspond to the name of an individual, rather than the first candidate word "John" being a name and the second candidate word "Rock" corresponding to the geological object. By analyzing the context of the one or more candidate entry names with respect to one another, the application server 124 can disambiguate the one or more candidate entry names.

In some implementations, the application server 124 can utilize the identified one or more candidate entry names and the context information to retrieve data from the first distributed DB server 106 and the second distributed DB server 108. The application server 124 transmits data indicating a request for one or more entries in the first distributed DB server 106. The data indicating the request for one or more entries includes the one or more candidate entry names from the request 101. The data stored in the first distributed DB server 106 can be indexed by an entity name, as previously mentioned. Each field in an indexed row of the first distributed DB server 106 can include a visual object associated with the entity name. For example, a row indexed by the word "John" can include one or more fields of visual objects of the entity "John." The visual objects may include media, such as one or more pictures, one or more videos, or one or more scans, of the entity "John" over a period.

In addition, each field can include a corresponding time stamp indicating when the visual object of the entity was uploaded to the first distributed DB server 106. For example, one field can illustrate a visual object of the entity at a first point in time, such as Jan. 1, 2018 at 1:00 PM. Another field can illustrate another visual object of the entity at a second point in time, such as Feb. 1, 2018 at 1:00 PM. In other implementations, each field in a row of the first distributed DB server 106 can include additional information about the indexed entity. For example, if the indexed entity is a professional league sports team, the one or more fields can include the players of the sports team, a location of the sports team's stadium, a schedule of the sports team, the sports team's uniform, the sports team's mascot, and the coach's names.

In some implementations, the first distributed DB server 106 compares the one or more candidate entry names received from the application server 124 to the indexed names in the rows of a database of the first distributed DB server 106. In particular, the first distributed DB server 106 performs a text comparison between the one or more candidate entry names from the application server 124 to each of the entity names in a row of the database of the first distributed DB server 106. If the first distributed DB server 106 determines one or more matches exist in response to the text comparison, the first distributed DB server 106 provides the matched rows and corresponding fields to the application server 124. In some implementations, the application server 124 can retrieve data from the first distributed DB server 106 over a set time-period. For example, the application server 124 may request data from the first distributed DB server 106 over a time-period between Jan. 10, 2018 at 1:00 PM to Sep. 20, 2018 and 1:00 PM.

In response to the first distributed DB server 106 receiving the entity name and the set time-period, the first distributed DB server 106 can return data to the application server 124 that meets the requested criteria. For example, as shown in FIG. 1, the first distributed DB server 106 identifies a row of data that includes three visual objects for the request 101 "John" entity. In particular, the row of data includes visual object 112, visual object 114, and visual object 116.

In some implementations, the first distributed DB 106 server can prepare a visual object for delivery by associating metadata with the visual object that can be used by the application server 124 to correlate the visual object with other data records associated with the user. By way of example, the first distributed DB 106 may associate a timestamp with the visual object. For example, visual object 112 includes timestamp $T_0$ 112a, visual object 114 includes timestamp $T_1$ 114a, and visual object 116 includes timestamp $T_2$ 116a. The timestamp may describe, for example, the time, date, or both, when the visual object was first captured or the time date or both when the visual object was first stored in the first distributed DB 106.

In this example, the retrieved row of visual objects could depict X-RAY images of the entity "John" over a period. John may have a broken rib cage and a doctor can monitor the entity's healing process over time. For example, visual object 112 illustrates John's rib cage at a time 112a of Apr. 20, 2018 at 1:00 PM, visual object 114 illustrates John's rib cage at a time 114a of Jul. 20, 2018 at 1:00 PM, and visual object 116 illustrates John's rib cage at a time 116a of Sep. 20, 2018 at 1:00 PM. The doctor can use the visual object data from the entity's progress to watch how the entity progresses or digresses.

In some implementations, the first distributed DB server 106 transmits the visual object data 112, 114, and 116 to the application server 124, in response to receiving and processing the data indicating a request for one or more entries from the first distributed DB server 106. The first distributed DB server 106 transmits data indicative of the collective visual object data over the network 110 to the application server 124. For example, the data indicative of the collective visual object data can be a symbolic link to the visual object data 112, 114, and 116, the individual visual object data itself, or a data structure containing each of the visual object data 112, 114, and 116. In addition, the first distributed DB server 106 transmits metadata to the application server 124 corresponding to the indexed entity from the retrieved row. For example, the metadata can include data indicated by a doctor when the picture was uploaded regarding the entity's progress, context information regarding how the injury occurred, current programs entity is undergoing to aid in healing injury, and any similar data that relates to the entity.

The application server 124 transmits a request for data from the second distributed DB server 108. The request for data can include information from the request 101, metadata retrieved from the response by the first distributed DB server 106, or a combination of both. The data in the second distributed DB server 108 includes scores corresponding to a state of an entity at a particular time when a particular questionnaire completed for the entity and can be indexed by an entity name, similar to the data in the first distributed DB server 106. By way of example, a row of fields corresponding to the entity "John" can include a score 118 of "49", a score 120 of "58", and a score 122 of "53."

In some implementations, the scores may be percentages that indicate a health rating of the entity. For example, the scores can be numbers that indicate a score of an entity's range of motion of a particular body part, an entity's healing state of an injury, or an entity's overall health score. Each field in the row includes a respective timestamp that indicates a time when the entity was scored to determine the state of the entity. By way of example, an individual can enter in the scores for the state of the entity using the second distributed computer 104. In response, the second distributed computer 104 stores the scores in the second distributed DB server 108. For example, a doctor can score the state of an entity's range of motion of his right shoulder to "53" at a time 112a of Apr. 20, 2018 at 1:00 PM. In another example, the doctor can score the state of a patient's range of motion of his right shoulder to "58" at a time 114a of Jul. 20, 2018 at 1:00 PM. In another example, the doctor can score the state of an entity's range of motion of his right shoulder to "49" at a time 116a of Sep. 20, 2018 at 1:00 PM. In other implementations, the second distributed computer 104 may generate a score for an entity (e.g., a patient) based on questions and answers to one or more questionnaires.

In some implementations, the second distributed DB server 108 transmits the scores 118, 120, and 122 to the application server 124, in response to receiving and processing the data indicating a request for one or more entries from the second distributed DB server 108 and determining a match exists. The second distributed DB server 108 transmits data indicative of the collective scores over the network 110 to the application server 124 that match the data indicated in the request. For example, the data indicative of the collective visual scores can be the scores 118, 120, and 122 and corresponding timestamps 116a, 114a, and 112a, a link to the scores 118, 120, and 122 and corresponding timestamps 116a, 114a, and 112a, or the like. In addition, the second distributed DB server 108 may also transmits metadata corresponding to the indexed entity from the retrieved row of scores. For example, the metadata can include data indicated by a doctor that describe how the doctor determined the score for the entity, context information regarding how the entity has progressed or digressed since the last visit, and when the entity will next visit the doctor.

In some implementations, in response to the application server 124 receiving the visual object data 112, 114, and 116 and timestamps 112a, 114a, 116a from the first distributed DB server 106 and the score data 118, 120, and 122 and timestamps 118a, 120a, 122a from the second distributed DB server 108, the API 128 of the application server 124 executes software to correlate the two sets of data from distributed DB server 106, 108. Correlating the two sets of data from different distributed data DB servers 106, 108 may include using the API 128 aligning the visual object data 112, 114, and 116 from a first distributed DB server 106 with corresponding score data 118, 120, and 122 determined by a second distributed DB server 108 that is different than the first distributed DB server 106. The API 128 combines the data sets from different distributed DB servers 106, 108 using the timestamps as a basis for the alignment. For example, in the example of FIG. 1, the API 128 creates correlated data 130, 132, and 134 comprised of visual object data from a first distributed DB server 106 and score data from a second distributed DB server 108. In particular, the API 128 aligns visual object data 112 with the score 122 data because both correspond to time $T_0$. Similarly, API 128 aligns visual object data 114 with the score 120 because both correspond to time $T_1$ and aligns visual object data 116 with the score 118 because both correspond to time $T_2$.

Though precise matching of times $T_0$, $T_1$, and $T_2$, is used in this example, please note that the present disclosure need not be so limited. In some implementations, a visual object may be correlated and aligned with a score if the different times associated with the visual object and score fall within a predetermined time period such as the same day, same week, same month, same treatment cycle, or the like. Accordingly, it is possible for a visual object to be correlated with a score having a different timestamp than the visual object so long as the two respective time stamps satisfy a predetermined time period.

For example, the API 128 can set a predetermined time period to be 2 days. Thus, if the API 128 determines that visual object 112 includes a time T0 of Jan. 2, 2018 at 12:00 PM and if score 118 includes a time T2 of Jan. 3, 2018 at 12:00 PM, then the API will correlate visual object 112 with score 118. In some implementations, the API 128 can set the predetermined time factor based on a factory preset. In other implementations, a user can set the predetermined time factor by accessing the application server 124 through either the first distributed computer 102, the second distributed computer 104, or the client device 140. In other implementations, the API 128 may determine a predetermined time factor by analyzing times of previous uploads of visual object data and score data and averaging the times.

The API 128 uses the correlated visual object data and the score data to enhance the visual object data. In particular, the correlated visual object data and the score data 130, 132, 134 is used to generate other enhanced data sets. The other enhanced data sets can include trends, graphs over time, generated predictions, and other data analytical results. For instance, the API 128 may provide the correlated data 130, 132, and 134 to a trained machine-learning algorithm to provide a prediction of a future score at a future point in time. The API 128 can train the machine-learning algorithm with visual object data and scores of previous entities at previous points in time. In addition, the machine-learning algorithm can be trained to output a predicted score using the visual object data alone. In another example, the API 128 can plot the visual object data and scores on a graph to a show a trend in data over time. The x-axis indicates the times with which the application server 124 generated the scores. As illustrated in FIG. 1, API 128 generated the plot 138 that shows three respective points of the scores of an entity over time data that each correspond to the respective correlated data above. The plot 138 can be used to evaluate trends for an entity.

In some implementations, the API 128 generates rendering data 127 of the enhanced correlated data. In particular, the rendering data 127 provides a visual snapshot of the visual object data and the score data at corresponding times, as well as of the enhanced visual object data. For instance, the rendering data 127 illustrates the visual snapshot of data on one display page for easy to view accessibility. In some implementations, the API 128 can generate the rendering data in a 2D or 3D model. For example, the API 128 can adjust the shading, texture mapping, bump mapping, reflection, and transparency of objects on the visual image snapshot page. In addition, the rendering data 127 can include a screen-formatting feature to render the visual snapshot of data to fit on a screen size of a particular device, such as client device 140. Otherwise, the particular device may not properly display the visual snapshot data properly.

In some implementations, the API 128 transmits the rendering data 127 to the client device 140. The rendering data 127 is transmitted to the client device 140 over network 126. The client device 140 receives the rendering data 127, renders the rendering data 127, and displays the graphical user interface 136 that is generated based on the rendering of rendering data for a user. The user can interact with the various components of the graphical user interface 136 using a stylus or a finger. In particular, the user can rearrange the correlated data 130, 132, and 134 to a different order on the graphical user interface 136. In some implementations, the correlated data 130, 132, 134 is organized chronologically from left to right based on timestamp.

In some implementations, however, the user can move the placement of the plot 138 to another spot on the graphical user interface. The user can select a point on the plot 138 for the graphical user interface 136 to display additional information regarding that point. For example, if a user selected plot point 139 on the plot 138, the graphical user interface 136 would subsequently display an additional box that further displays the metadata corresponding to the score and virtual object of the correlated data 132. In response to a selection to interact with a component on the client device 140, the client device 140 transmits the selection to the API 128 of the application server 124. The API 128 processes the received selection and transmits the requested information back to the client device 140. For example, if the user selected plot point 139 on the plot 138, the graphical user interface 136 would transmit the selection of the plot point 139 to the API 128 over the network 126. The API 128 would receive the selection of the plot point 139 and transmit the metadata information corresponding to the selected plot point 139 to the client device 140 for display. In other implementations, the client device 140 would include the metadata and would process the selection of a plot point without having to transmit a request to the API 128.

The distributed fashion of the system described with reference to the example of FIG. 1 provides multiple advantages. For example, the system permits multiple, distributed source computers to create, process, and manage records close to their source until being accessed by a centralized manager such as the application server 124. As necessary, the application server can obtain and correlate data from each distributed system, or a portion thereof, in a manner that reduces the amount of bandwidth necessary to respond to a user request.

Importantly, the distributed nature of the data creation, data gathering, data filtering, and data searching that is achieved by the system of FIG. 1 enables load distribution. Each particular source computer can solely generate, access, and manipulate data granularly by only interacting with the data associated with the particular source. This helps to use available network bandwidth more efficiently. For example, instead of a computer 102 and 104 needing to create, access, and manipulate data in a central data store, each respective computer can create, access, and manipulate data at their node of a distribute network that avoids the congestion of a single network bottleneck at a centralized server.

On the other hand, the correlation of data records by the application server enables the system 100 to provide all the benefits of a centralized storage location—e.g., a single repository that can receive a single query and provide a single set of search results that a user needs responsive to a query without the drawbacks of a massive record flows through a single network bottleneck. Moreover, implementing a system where a query from a single user interface can search multiple disparate databases and result in a single set of search results being received in a single interface on a client device is more resource efficient for the client device than a system that would require a user device to use multiple interfaces, multiple applications, and submit multiple queries yielding multiple results. Thus, the user device using the system 100 can use less system resources due to the nature of the system 100.

Finally, the distributed fashion of the system 100 also provides additional advantages for network devices and data gatherers. Though the system described in FIG. 1 only includes two distributed data sources, the present disclosure need not be so limited, instead, the application server 124 may correlate data records from three, four, five, or many more data sources based on timestamps, as described above with reference to correlating of records from the first distributed DB server 106 and the second distributed DB server 108. In such cases, a response to a user query may only call for certain data. For example, the query may have parameters specifying that only a score and visual object should be returned and not entity records describing the entity's vaccination history, which may be stored in a third distributed database. Which data sources to search and include may be specified using, e.g., radio buttons. In such instances, the distributed nature of the system 100 can help to meaningfully tailor execution of queries in order to conserve system resources (e.g., CPU usage, memory usage, bandwidth usage, power usage, etc.) while also generating an enhanced record that includes the information the user seeks.

Figure 2:
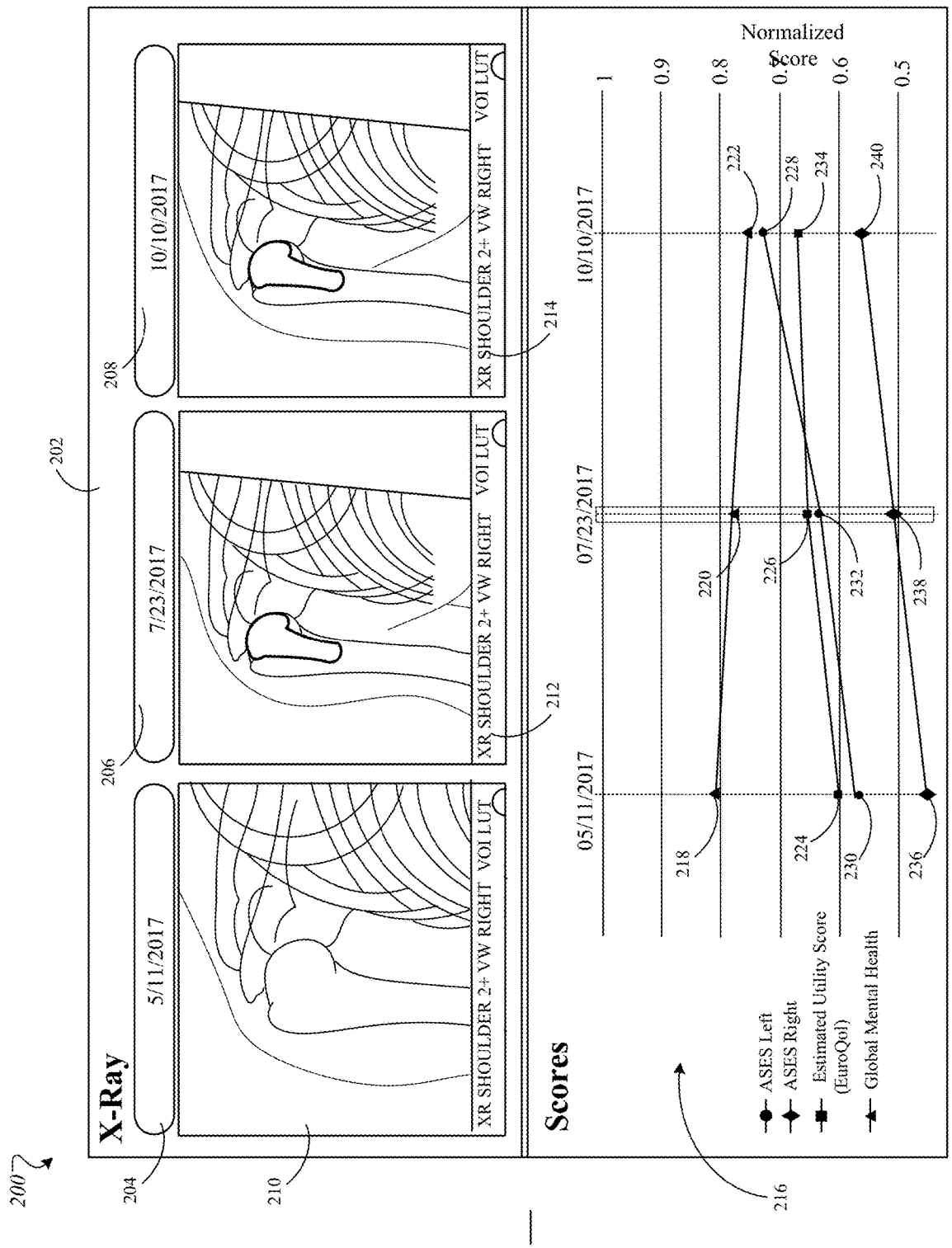
FIG. 2 is an example of a user interface of a visual snapshot of the correlated distributed database records.

FIG. 2 is an example of a user interface 200 of a visual snapshot of the correlated distributed database records.

In some implementations, the API 128 of the application server 124 generates rendering data of a visual snapshot to provide to a client device 140. The user interface 200 illustrates the rendering data that include overlays of layered data types. For example, the layered data types can include visual object data, textual data, coordinate system data, and interactive data. The user interface 200 shows an example of a user interface that client device 140 displays to a user. In particular, the user interface 200 includes a display panel 202 that includes visual object data 210, 212, and 214. Each visual object corresponds to time data 204, 206, and 208 when the visual object was captured. For example, the visual object 210 illustrates an X-RAY image of a right shoulder on a date 204 of May 11, 2017. The visual object 212 illustrates an X-RAY image of the same right shoulder on a date 206 of Jul. 23, 2017. The visual object 214 illustrates an X-RAY image of the same right shoulder at a date 208 of Oct. 10, 2017.

In addition, the display panel 202 includes a coordinate system panel 216. The coordinate system panel 216 includes a plot of corresponding data points for each particular visual object at a point in time. For example, the coordinate system panel 216 illustrates various scores on May 11, 2017 corresponding to the visual object 210. In particular, the various scores correspond to different ratings used by medical practitioners to assess the health of the right shoulder. For example, score 218 corresponds to the Global Mental Health rating, score 224 corresponds to the Estimated Utility Score (EuroQol) rating, score 230 corresponds to the American Shoulder and Elbow Surgeons (ASES) Left rating, and score 236 corresponds to the ASES Right rating.

At a second date, Jul. 23, 2017, the entity's right shoulder is reevaluated using the same various ratings. For example, the plot illustrates that on Jul. 23, 2017, score 220 corresponding to the Global Mental Health rating has dropped since the last evaluation of score 218 on May 11, 2017. Score 226 corresponding to the EuroQol rating has increased since the last evaluation of score 224 on May 11, 2017. Score 232 corresponding to the ASES Left rating has increased since the last evaluation of score 230 on May 11, 2017. Score 238 corresponding to the ASES Right rating has increase since the last evaluation of score 236 on May 11, 2017.

At a third date, Oct. 10, 2017, the entity's right shoulder is reevaluated using the same various ratings. For example, the plot illustrates that on Oct. 10, 2017, score 222 corresponding to the Global Mental Health rating has dropped since the last evaluation of score 220 on Jul. 23, 2017. Score 228 corresponding to the ASES Left rating has increased since the last evaluation of score 232 on Jul. 23, 2017. Score 234 corresponding to the EuroQol rating has increased since the last evaluation of score 226 on Jul. 23, 2017. Score 240 corresponding to the ASES Right rating has increased since the last evaluation of score 238 on Jul. 23, 2017. Generally, an increase in score over time indicates that the entity's body part is improving in health, functionality, or both. Likewise, a decrease in score over time indicates that the entity's body part is deteriorating in health, functionality, or both. In some implementations, the corresponding system panel may plot the scores in a normalized score system. For example, the application server 124 may normalize the scores by dividing the scores by 100 to plot on a scale from 0 to 1. In other implementations, the application server 124 may plot the non-normalized scores on the coordinate system panel 216.

Though the graphical user interface 200 is related to X-ray images and entity scores, the present disclosure need not be so limited. For example, images of real-estate properties could be correlated with scores to highlight a score trend corresponding to an image of the real-estate property over time. Accordingly, the correlating other types of objects or entities with other types of scores to generate enhanced data records for display also fall within the scope of the present disclosure.

Figure 3:
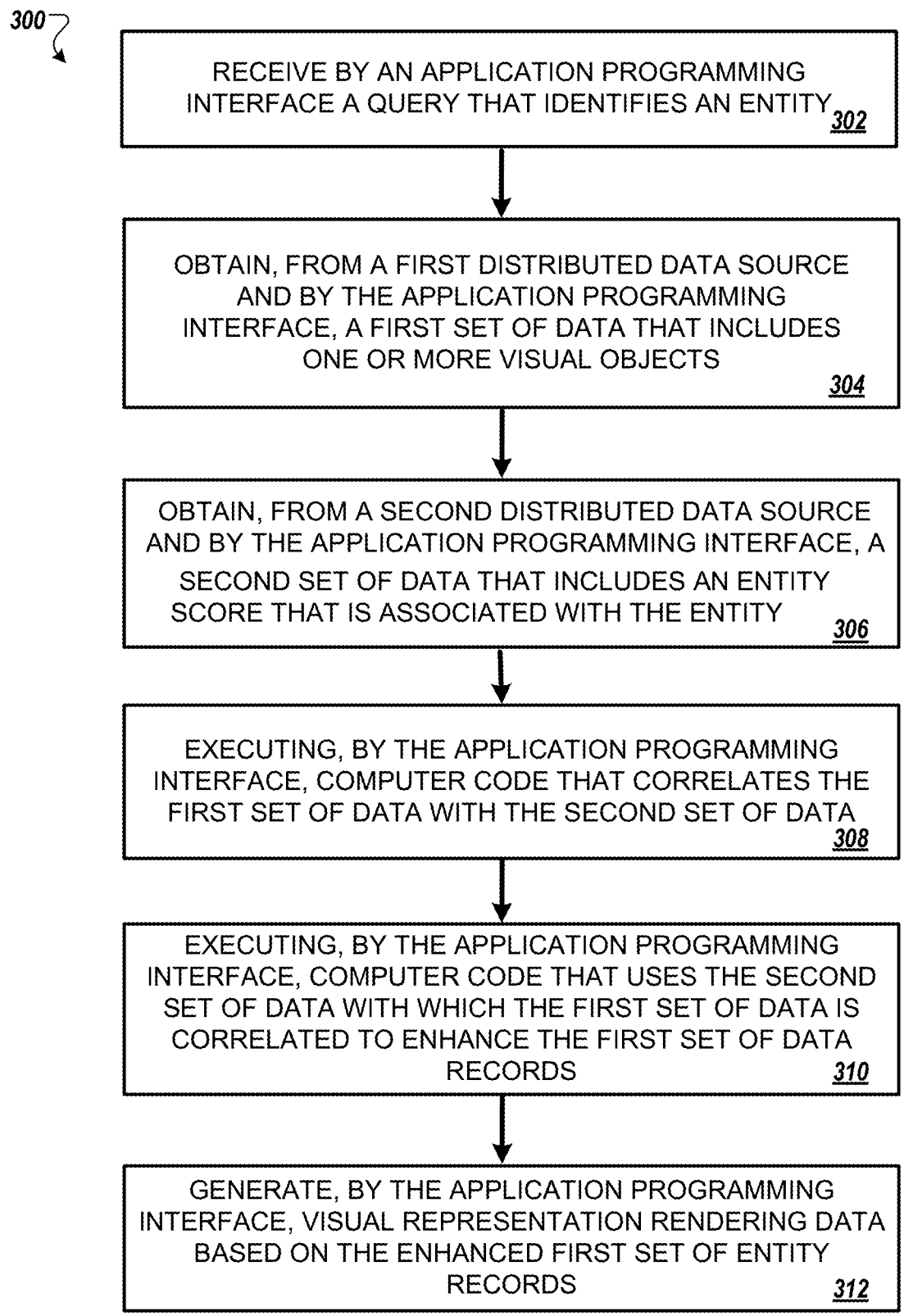
FIG. 3 is a flowchart of an example process for illustrating a visual snapshot of the correlated distributed database records.

FIG. 3 is a flowchart of an example process 300 for illustrating a visual snapshot of the correlated distributed database records. Generally, the process 300 includes receiving by an application programming interface a query that identifies an entity; obtaining, from a first distributed data source and by the application programming interface, a first set of data structures representing data records having fields including one or more visual objects that are responsive to the query; obtaining, from a second distributed data source and by the application programming interface, a second set of data structures that includes one or more records representing a state of the entity; executing, by the application programming interface, computer code that correlates the first set of data records represented by the first set of data structures with the second set of data records represented by the second set of data structures; executing, by the application programming interface, computer code that uses the correlated data to enhance the first set of data records; and generating, by the application programming interface, visual representation rendering data based on the enhanced first set of entity records. Alternatively, the process 300 can be used for interacting with the visual representation rendering data that includes the enhanced first set of entity records, for example. The process 300 will be described as being performed by a computer system comprising one or more computers, for example, the system 100 as shown in FIG. 1.

During 302, the system receives, by an application programming interface, a query 101 that identifies an entity. A user can interact with a client device 140 to send a query 101 to the system, where the query identifies the entity. For example, a doctor can enter a request for an entity "John" into an application of a client device 140. The client device 140 transmits the query with the entity "John" to the application programming interface 128 of the system for processing. The application programming interface 128 receives the query 101 and identifies the entity "John" in the query 101.

During 304, the system obtains, from a first distributed data source and by the application programming interface, a first set of data structures representing data records having fields including one or more visual objects that are responsive to the query. The system then utilizes one or more candidate entry names that are identified based on the received query to access and retrieve data from the first distributed data source, such as the first distributed DB server 106. Each field in an indexed row of the first distributed DB server 106 can include a visual object of the entity name. For example, one field can illustrate a graphical object of the entity at a first point in time, such as Jan. 1, 2018 at 1:00 PM. Another field can illustrate another visual object of the entity at a second point in time, such as Feb. 1, 2018 at 1:00 PM.

In some implementations, the first distributed DB server 106 compares the received candidate entry names to the indexed entities in each row of the first distributed DB server 106. In particular, the first distributed DB server 106 performs a text comparison between the candidate entry names from the application server 124 to each of the entity names in a row of the database of the first distributed DB server 106. If the first distributed DB server 106 determines one or more matches exist in response to the text comparison, the first distributed DB server 106 provides the matched rows and corresponding fields to the application server 124.

During 306, the system obtains, from a second distributed data source and by the application programming interface, a second set of data structures representing that includes one or more records representing a state of an entity. In some implementations, the state of an entity may be represented using a score. The system transmits a request for data from the second distributed data source, such as the second distributed DB server 108. The request for data can include information from the request 101 and metadata retrieved from the response by the first distributed DB server 106. The data in the second distributed DB server 108 can be indexed by an entity name, similar to the data in the first distributed DB server 106. The data stored in the second distributed DB server 108 includes scores corresponding to a state of the entity. For example, a row of fields corresponding to the entity "John" can include a score 118 of "49", a score 120 of "58", and a score 122 of "53." In some implementations, the scores can be percentages that indicate a health rating of the entity. For example, the scores can be numbers that indicate a score of an entity's range of motion of a particular body part, an entity's healing state of an injury, or an entity's overall health score.

In response to determining a match between the data in the request and one or more rows in the second distributed DB server 108, the second distributed DB server 108 transmits the scores to the application server 124. In addition, the second distributed DB server 108 transmits metadata corresponding to the indexed entity from the retrieved row of scores. For example, the metadata can include data indicated by a doctor that describe how the doctor determined the score for the entity, context information regarding how the entity has progressed or digressed since the last visit, and when the entity will next visit the doctor.

During 308, the system executes, by the application programming interface, computer code that correlates the first set of data records represented by the first set of data structures with the second set of data records represented by the second set of data structures. In response to receiving the visual object data from the first distributed DB server 106 and the score data from the second distributed DB server 108, the API executes software to correlate this data. In particular, the API correlates the visual object data and the score data over a time period by aligning the data sets. In some implementations, the API can receive the first set of data from the first distributed DB server 106 and a second set of data from the second distributed DB server 108, and perform the correlating of the search results on the application server 124. The API combines the data sets using the time period as a basis for the alignment. For example, the API 128 creates correlated data 130, 132, and 134 of the visual object and score data. In particular, the API 128 aligns visual object data 112 with the score 122 data because both correspond to time $T_0$. Similarly, API 128 aligns visual object data 114 with the score 120 because both correspond to time $T_1$ and aligns visual object data 116 with the score 118 because both correspond to time $T_2$.

During 310, the system executes, by the application programming interface, computer code that uses the correlated data to enhance the first set of data records. In particular, the API generates enhanced data by generating other data sets for a user to view. For instance, the other data sets can include trends, graphs over time, generated predictions, and other data analytical results. For instance, the API 128 may provide the correlated data 130, 132, and 134 to a trained machine-learning algorithm to provide a prediction of a future score at a future point in time. In addition, the machine-learning algorithm can be trained to output a predicted score using the visual object data alone. In another example, the API 128 can plot the visual object data and scores on a graph to a show a trend in data over time. The x-axis indicates the times with which the application server 124 generated the scores. As illustrated in FIG. 1, API 128 generated the plot 138 that shows three points of the scores of an entity over time data.

During 312, the system generates, by the application programming interface, visual representation rendering data based on the enhanced first set of entity records. The API generates rendering data of the enhanced data that illustrates a visual snapshot of the visual object data and the score data at corresponding times, as well as of the enhanced visual object data. For instance, the rendering data 127 illustrates the visual snapshot of data on one display page for easy to view accessibility on client device 140. In response to generating the visual representation rendering data, the application programming interface transmits the visual representation rendering data to client device 140 for display.

Figure 4:
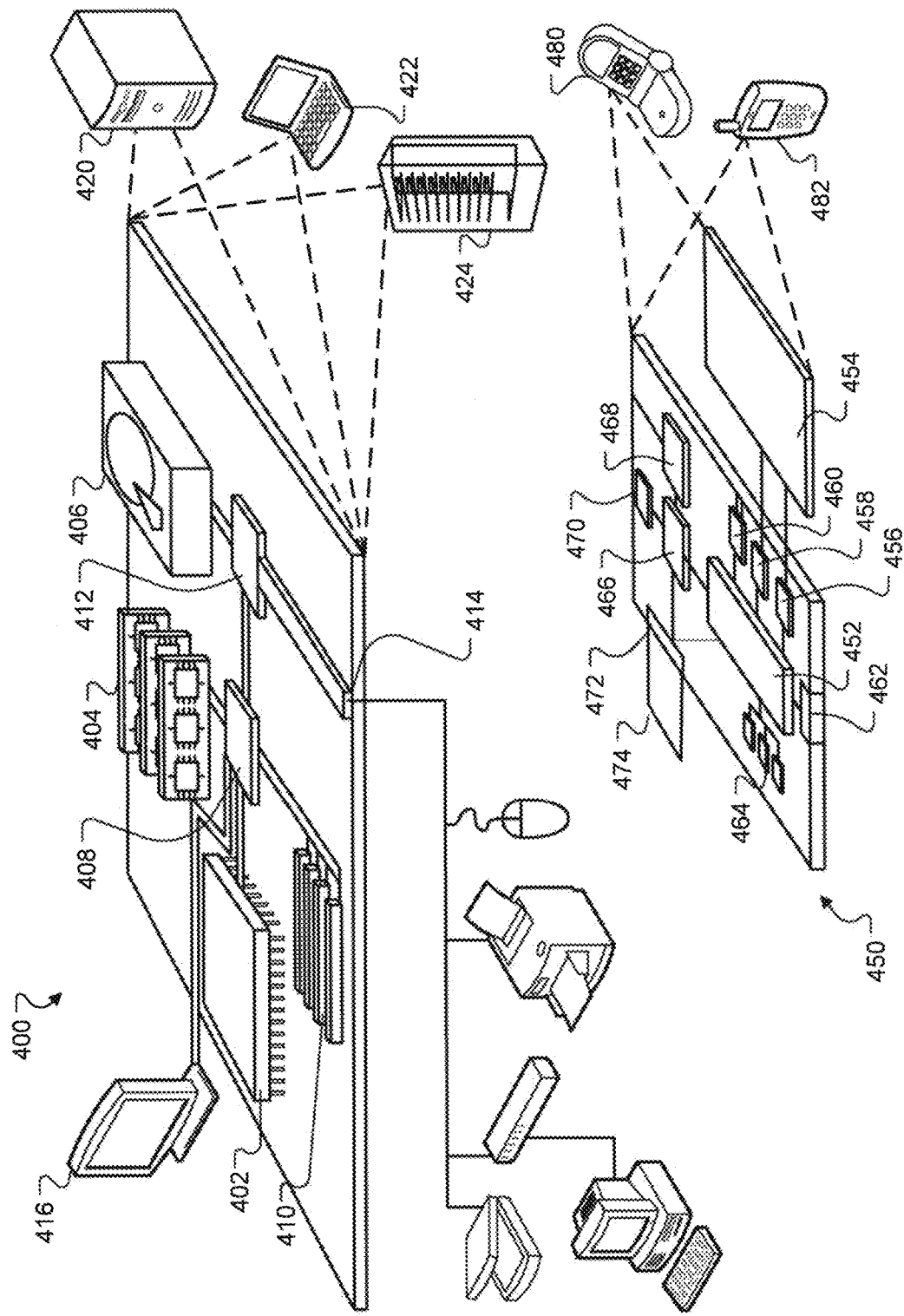
FIG. 4 shows an example of a computing device and a mobile computing device.

FIG. 4 shows an example of a computing device 400 and a mobile computing device 450 that can be used to implement the techniques described here.

The computing device 400 is intended to represent various forms of digital computers, such as laptops, desktops, workstations, personal digital assistants, servers, blade servers, mainframes, and other appropriate computers. The mobile computing device 450 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 400 includes a processor 402, a memory 404, a storage device 406, a high-speed interface 408 connecting to the memory 404 and multiple high-speed expansion ports 410, and a low-speed interface 412 connecting to a low-speed expansion port 414 and the storage device 406. Each of the processor 402, the memory 404, the storage device 406, the high-speed interface 408, the high-speed expansion ports 410, and the low-speed interface 412, are interconnected using various busses, and may be mounted on a common motherboard or in other manners as appropriate. The processor 402 can process instructions for execution within the computing device 400, including instructions stored in the memory 404 or on the storage device 406 to display graphical information for a GUI on an external input/output device, such as a display 416 coupled to the high-speed interface 408. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 404 stores information within the computing device 400. In some implementations, the memory 404 is a volatile memory unit or units. In some implementations, the memory 404 is a non-volatile memory unit or units. The memory 404 may also be another form of computer-readable medium, such as a magnetic or optical disk.

The storage device 406 is capable of providing mass storage for the computing device 400. In some implementations, the storage device 406 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 402), perform one or more methods, such as those described above. The instructions can also be stored by one or more storage devices such as computer- or machine-readable mediums (for example, the memory 404, the storage device 406, or memory on the processor 402).

The high-speed interface 408 manages bandwidth-intensive operations for the computing device 400, while the low-speed interface 412 manages lower bandwidth-intensive operations. Such allocation of functions is an example only. In some implementations, the high-speed interface 408 is coupled to the memory 404, the display 416 (e.g., through a graphics processor or accelerator), and to the high-speed expansion ports 410, which may accept various expansion cards (not shown). In the implementation, the low-speed interface 412 is coupled to the storage device 406 and the low-speed expansion port 414. The low-speed expansion port 414, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 420, or multiple times in a group of such servers. In addition, it may be implemented in a personal computer such as a laptop computer 422. It may also be implemented as part of a rack server system 424. Alternatively, components from the computing device 400 may be combined with other components in a mobile device (not shown), such as a mobile computing device 450. Each of such devices may contain one or more of the computing device 400 and the mobile computing device 450, and an entire system may be made up of multiple computing devices communicating with each other.

The mobile computing device 450 includes a processor 452, a memory 464, an input/output device such as a display 454, a communication interface 466, and a transceiver 468, among other components. The mobile computing device 450 may also be provided with a storage device, such as a micro-drive or other device, to provide additional storage. Each of the processor 452, the memory 464, the display 454, the communication interface 466, and the transceiver 468, are interconnected using various buses, and several of the components may be mounted on a common motherboard or in other manners as appropriate.

The processor 452 can execute instructions within the mobile computing device 450, including instructions stored in the memory 464. The processor 452 may be implemented as a chipset of chips that include separate and multiple analog and digital processors. The processor 452 may provide, for example, for coordination of the other components of the mobile computing device 450, such as control of user interfaces, applications run by the mobile computing device 450, and wireless communication by the mobile computing device 450.

The processor 452 may communicate with a user through a control interface 458 and a display interface 456 coupled to the display 454. The display 454 may be, for example, a TFT (Thin-Film-Transistor Liquid Crystal Display) display or an OLED (Organic Light Emitting Diode) display, or other appropriate display technology. The display interface 456 may comprise appropriate circuitry for driving the display 454 to present graphical and other information to a user. The control interface 458 may receive commands from a user and convert them for submission to the processor 452. In addition, an external interface 462 may provide communication with the processor 452, so as to enable near area communication of the mobile computing device 450 with other devices. The external interface 462 may provide, for example, for wired communication in some implementations, or for wireless communication in other implementations, and multiple interfaces may also be used.

The memory 464 stores information within the mobile computing device 450. The memory 464 can be implemented as one or more of a computer-readable medium or media, a volatile memory unit or units, or a non-volatile memory unit or units. An expansion memory 474 may also be provided and connected to the mobile computing device 450 through an expansion interface 472, which may include, for example, a SIMM (Single In Line Memory Module) card interface. The expansion memory 474 may provide extra storage space for the mobile computing device 450, or may also store applications or other information for the mobile computing device 450. Specifically, the expansion memory 474 may include instructions to carry out or supplement the processes described above, and may include secure information also. Thus, for example, the expansion memory 474 may be provided as a security module for the mobile computing device 450, and may be programmed with instructions that permit secure use of the mobile computing device 450. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier, such that the instructions, when executed by one or more processing devices (for example, processor 452), perform one or more methods, such as those described above. The instructions can also be stored by one or more storage devices, such as one or more computer- or machine-readable mediums (for example, the memory 464, the expansion memory 474, or memory on the processor 452). In some implementations, the instructions can be received in a propagated signal, for example, over the transceiver 468 or the external interface 462.

The mobile computing device 450 may communicate wirelessly through the communication interface 466, which may include digital signal processing circuitry where necessary. The communication interface 466 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 468 using a radio-frequency. In addition, short-range communication may occur, such as using a Bluetooth, WiFi, or other such transceiver (not shown). In addition, a GPS (Global Positioning System) receiver module 470 may provide additional navigation- and location-related wireless data to the mobile computing device 450, which may be used as appropriate by applications running on the mobile computing device 450.

The mobile computing device 450 may also communicate audibly using an audio codec 460, which may receive spoken information from a user and convert it to usable digital information. The audio codec 460 may likewise generate audible sound for a user, such as through a speaker, e.g., in a handset of the mobile computing device 450. Such sound may include sound from voice telephone calls, may include recorded sound (e.g., voice messages, music files, etc.) and may also include sound generated by applications operating on the mobile computing device 450.

The mobile computing device 450 may be implemented in a number of different forms, as shown in the figure. For example, it may be implemented as a cellular telephone 480. It may also be implemented as part of a smart-phone 482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Although a few implementations have been described in detail above, other modifications are possible. For example, while a client application is described as accessing the delegate(s), in other implementations the delegate(s) may be employed by other applications implemented by one or more processors, such as an application executing on one or more servers. In addition, the logic flows depicted in the figures do not require the particular order shown, or sequential order, to achieve desirable results. In addition, other actions may be provided, or actions may be eliminated, from the described flows, and other components may be added to, or removed from, the described systems. Accordingly, other implementations are within the scope of the following claims.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A computer-implemented method for generating visual snapshot rendering data that, when rendered by a user device, provides a visual snapshot that describes a historical trend associated with an entity that correlates multiple data records from different distributed data sources into a single user interface of an application, the method comprising:
    receiving, by an application programming interface and from the user device, a query, wherein the query comprises an entity identifier and one or more parameters specifying at least one type of numerical score and at least one type of visual object as the data to be obtained;
    obtaining, by the application programming interface, a first set of data structures representing first entity records from a first distributed data source that are responsive to the query, wherein each of the first entity records comprises a visual object that is responsive to the query and associated with a first time when the visual object was generated;
    obtaining, by the application programming interface, a second set of data structures representing second entity records from a second distributed data source that are responsive to the query, wherein each of the second entity records comprises an entity numerical score that is associated with a second time when the entity numerical score was generated;
    executing, by the application programming interface, computer program code that correlates the first entity records represented by the first set of data structures from the first distributed data source with the second entity records represented by the second set of data structures from the second distributed data source based on the first time and the second time;
    determining a difference between the first time and the second time satisfies a threshold corresponding to a range of time;
    generating, by the application programming interface, a new correlated data set that includes the visual object associated with the first time and the entity numerical score associated with the second time based on correlating the visual object of the first entity records with the numerical score of the second entity records, wherein the visual object of the first entity records and the numerical score of the second entity records are correlated based on a determination that the first time and the second time each fall within the threshold corresponding to the range of time;
    executing, by the application programming interface, computer program code that enhances the first entity records, wherein enhancing the first entity record comprises combining the new correlated data set with the first entity records; and
    generating, by the application programming interface, visual snapshot rendering data using the enhanced first entity records, wherein the visual snapshot rendering data includes rendering data that, when rendered by the user device, causes a display of the user device to display the visual object and the numerical score.

2. The computer-implemented method of claim 1, wherein the entity numerical score, for each entity record of the second entity records, is based on answers provided to questions of a questionnaire.

3. The computer-implemented method of claim 1, wherein the visual object includes an image of one or more portions of the entity.

4. The computer-implemented method of claim 1, wherein executing, by the application programming interface, computer program code that correlates the first entity records represented by the first set of data structures from the first distributed data source with the second entity records represented by the second set of data structures from the second distributed data source based on the first time and the second time comprises:
    for each particular entity record of the first set of entity records:
        correlating the particular entity record with one or more of the second entity records from the second distributed data source based on a determination that the first time and the second time both fall within a predetermined time period.

5. The computer-implemented method of claim 1, further comprising:
    in response to generating the visual snapshot rendering data based on the enhanced first entity records, transmitting, by the application programming interface, the visual snapshot rendering data to the user device for display.

6. The computer-implemented method of claim 5, further comprising:
    receiving, by the application programming interface, a user selection on a plot point of the visual snapshot rendering data for a request for metadata corresponding to a particular visual object and a corresponding time; and
    transmitting, by the application programming interface, the metadata corresponding to the particular visual object and the corresponding time to the user device for display.

7. A system comprising:
    one or more computers and one or more storage devices storing instructions that are operable, when executed by the one or more computers, to cause the one or more computers to perform operations to generate visual snapshot rendering data that, when rendered by a user device, provides a visual snapshot that describes a historical trend associated with an entity that correlates multiple data records from different distributed data sources into a single user interface of an application, the operations comprising:
        receiving, by an application programming interface and from the user device, a query, wherein the query comprises an entity identifier and one or more parameters specifying at least one type of numerical score and at least one type of visual object as the data to be obtained;
        obtaining, by the application programming interface, a first set of data structures representing first entity records from a first distributed data source that are responsive to the query, wherein each of the first entity records comprises a visual object that is responsive to the query and associated with a first time when the visual object was generated;

obtaining, by the application programming interface, a second set of data structures representing second entity records from a second distributed data source that are responsive to the query, wherein each of the second entity records comprises an entity numerical score that is associated with a second time when the entity numerical score was generated;

executing, by the application programming interface, computer program code that correlates the first entity records represented by the first set of data structures from the first distributed data source with the second entity records represented by the second set of data structures from the second distributed data source based on the first time and the second time;

generating, by the application programming interface, a new correlated data set that includes the visual object associated with the first time and the entity numerical score associated with the second time based on correlating the visual object of the first entity records with the numerical score of the second entity records, wherein the visual object of the first entity records and the numerical score of the second entity records are correlated based on a determination that the first time and the second time each fall within the threshold corresponding to the range of time;

executing, by the application programming interface, computer program code that enhances the first entity records, wherein enhancing the first entity record comprises combining the new correlated data set with the first entity records; and generating, by the application programming interface, visual snapshot rendering data using the enhanced first entity records, wherein the visual snapshot rendering data includes rendering data that, when rendered by the user device, causes a display of the user device to display the visual object and the numerical score.

8. The system of claim 7, wherein the entity numerical score, for each entity record of the second entity records, is based on answers provided to questions of a questionnaire.

9. The system of claim 7, wherein the visual object includes an image of one or more portions of the entity.

10. The system of claim 7, wherein the visual object includes a video of the entity.

11. The system of claim 7, wherein executing, by the application programming interface, computer program code that correlates the first entity records represented by the first set of data structures from the first distributed data source with the second entity records represented by the second set of data structures from the second distributed data source comprises:

for each entity record of the first entity records:
correlating the entity record with one or more of the second entity records from the second distributed data source based on a determination that the first time and the second time both fall within a predetermined time period.

12. The system of claim 7, further comprising:
in response to generating the visual snapshot rendering data based on the enhanced first entity records, transmitting, by the application programming interface, the visual snapshot rendering data to the user device for display.

13. The system of claim 12, further comprising:
receiving, by the application programming interface, a user selection on a plot point of the visual snapshot rendering data for a request for metadata corresponding to a particular visual object and a corresponding time; and transmitting, by the application programming interface, the metadata corresponding to the particular visual object and the corresponding time to the user device for display.

14. The system of claim 7, wherein the visual snapshot rendering data is modeled in a 3D format.

15. A non-transitory computer-readable medium storing software comprising instructions executable by one or more computers which, upon such execution, cause the one or more computers to perform operations to generate visual snapshot rendering data that, when rendered by a user device, provides a visual snapshot that describes a historical trend associated with an entity that correlates multiple data records from different distributed data sources into a single user interface of an application, operations comprising:

receiving, by an application programming interface and from the user device, a query, wherein the query comprises an entity identifier and one or more parameters specifying at least one type of numerical score and at least one type of visual object as the data to be obtained;

obtaining, by the application programming interface, a first set of data structures representing first entity records from a first distributed data source that are responsive to the query, wherein each of the first entity records comprises a visual object that is responsive to the query and associated with a first time when the visual object was generated;

obtaining, by the application programming interface, a second set of data structures representing second entity records from a second distributed data source that are responsive to the query, wherein each of the second entity records comprises an entity numerical score that is associated with a second time when the entity numerical score was generated;

executing, by the application programming interface, computer program code that correlates the first entity records represented by the first set of data structures from the first distributed data source with the second entity records represented by the second set of data structures from the second distributed data source based on the first time and the second time;

generating, by the application programming interface, a new correlated data set that includes the visual object associated with the first time and the entity numerical score associated with the second time based on correlating the visual object of the first entity records with the numerical score of the second entity records, wherein the visual object of the first entity records and the numerical score of the second entity records are correlated based on a determination that the first time and the second time each fall within the threshold corresponding to the range of time;

executing, by the application programming interface, computer program code that enhances the first entity records, wherein enhancing the first entity record comprises combining the new correlated data set with the first entity records; and generating, by the application programming interface, visual snapshot rendering data using the enhanced first entity records, wherein the visual snapshot rendering data includes rendering data that, when rendered by the user device, causes a display of the user device to display the visual object and the numerical score.

16. The computer-readable medium of claim 15, wherein the entity numerical score, for each entity record of the second entity records, is based on answers provided to questions of a questionnaire.

17. The computer-readable medium of claim 15, wherein the visual object includes an image one or more portions of the entity.

18. The computer-readable medium of claim 15, wherein the visual object includes a video of the entity.

* * * * *